(12) United States Patent
Wang

(10) Patent No.: US 6,446,667 B1
(45) Date of Patent: Sep. 10, 2002

(54) BALL VALVE STRUCTURE

(76) Inventor: James Wang, 11Fl.-1, No. 45, Chungde 3rd Rd., Beituen Chiu, Taichung 406 (TW)

( * ) Notice: Subject to any disclaimer, the term of this patent is extended or adjusted under 35 U.S.C. 154(b) by 8 days.

(21) Appl. No.: 09/811,474

(22) Filed: Mar. 20, 2001

(51) Int. Cl.[7] .............................................. F16K 11/087
(52) U.S. Cl. ............................ 137/625.22; 137/625.47
(58) Field of Search ..................... 137/625.19, 625.22, 137/625.47

(56) References Cited

U.S. PATENT DOCUMENTS

| | | | | | |
|---|---|---|---|---|---|
| 679,071 | A | * | 7/1901 | Garnier | 137/625.22 |
| 1,327,252 | A | * | 1/1920 | Paulson | 137/625.47 |
| 3,684,241 | A | * | 8/1972 | Hartmann et al. | 251/315.13 |
| 4,548,237 | A | * | 10/1985 | Bogenschutz | 137/625.22 |
| 4,573,498 | A | * | 3/1986 | Ludwig | 137/625.47 |
| 4,915,133 | A | * | 4/1990 | Harrison | 137/625.47 |
| 5,988,220 | A | * | 11/1999 | Sakaki | 137/625.47 |
| 6,189,807 | B1 | * | 2/2001 | Miller et al. | 239/124 |

* cited by examiner

*Primary Examiner*—John Fox
(74) *Attorney, Agent, or Firm*—Rosenberg, Klein & Lee

(57) ABSTRACT

A ball valve includes a body, two side covers, a central shaft, a handle, a ball, and two ball pads. The ball defines a main flow hole and a secondary flow hole perpendicular to and is not communicated with the main flow hole. One ball pad defines a main passage hole and a secondary passage hole corresponding to the main flow hole and the secondary flow hole. One side cover defines a main through hole and a secondary through hole corresponding to the main passage hole and secondary passage hole. When the secondary flow hole, the secondary passage hole, and the secondary through hole communicate with each other, a fluid contained in a pipe is introduced to outside of the ball valve, so that the fluid contained the pipe can be sampled without having to dismantle the pipe, thereby facilitating a sampling work in each section of the pipe.

2 Claims, 6 Drawing Sheets

BALL VALVE STRUCTURE

BACKGROUND OF THE INVENTION

1. Field of the Invention

The present invention relates to a ball valve structure improvement, and more particularly to a ball valve structure improvement, wherein the fluid contained the pipe can be sampled without having to dismantle the pipe, thereby facilitating the sampling work in each section of the pipe.

2. Description of the Related Prior Art

A conventional ball valve structure in accordance with the prior art shown in FIG. 1 comprises a body 1, two side covers 2, a central shaft 3, a handle 4, a ball 5, and two ball pads 6.

The body 1 defines a receiving chamber 10 for receiving the ball 5 and the ball pads 6. The body 1 also defines a shaft hole 11 for pivoting of the central shaft 3. The side covers 2 each define a through hole 20, and are secured on the two sides of the body 1 by bolts 22 and nuts 23. A fitting ring 21 is mounted between the side cover 2 and the body 1 for preventing leakage. The central shaft 3 has a lower end extended into the body through a rotation ring 30 and inserted into the ball 5 for rotating the ball 5, and an upper end extended outward from the shaft hole 11 of the body 1 to in turn pass through rings 31, a set screw 32, the handle 4, a washer 33, and is screwed by a nut 34, so that the central shaft 3 can be rotated by the handle 4 to rotate the ball 5. The ball 5 defines a through hole 50 therein. The ball pads 6 are respectively mounted on the two sides of the ball 5, and each have one side facing the ball 5 and formed with an arc-shaped face 60 so that the ball 5 can be tightly inserted therein.

Thus, when the handle 4 is rotated to have the same direction as the flow path, the ball 5 is rotated by the rotation shaft 3 to a position where the through hole 50 communicates with the through hole 20 of each side cover 2, so that the flow path is disposed at an open state. On the contrary, when the ball 5 is rotated by the rotation shaft 3 to a position where the through hole 50 is not communicated with the through hole 20 of each side cover 2, the flow path is disposed at a closed state.

However, if the operator wishes to sample and inspect the fluid in the pipe, the fluid in the pipe has to be disposed at a stationary state or part of the pipe has to be closed. Then, proper valves are dismantled, so that the pipe of the sampling region is disposed at an open state. The pipe is then opened, so that the fluid can flow out for sampling. Thus, the pipe has to be assembled and dismantled frequently, thereby causing inconvenience to the operator, and thereby easily incurring the situation of leakage.

SUMMARY OF THE INVENTION

The present invention has arisen to mitigate and/or obviate the disadvantage of the conventional ball valve structure.

The primary objective of the present invention is to provide a ball valve structure improvement comprising: a body, a first side cover, a second side cover, a central shaft, a handle, a ball, a first ball pad, and a second ball pad, the first ball pad and the second ball pad respectively mounted on two sides of the ball, the central shaft having a first end extended into the body and inserted into the ball for rotating the ball, and a second end extended outward from the body and secured with the handle, the first side cover and the second side cover respectively mounted on two sides of the body, for sealing the ball, the first ball pad, and the second ball pad in the body, wherein, a main flow hole is defined through the ball, a secondary flow hole is eccentrically defined through the ball, the secondary flow hole is perpendicular to and is not communicated with the main flow hole, the second ball pad mounted on one side of the ball defines a main passage hole located at a position opposite to the main flow hole, and a secondary passage hole located at a position opposite to the secondary flow hole, the second side cover mounted beside the second ball pad defines a main through hole located at a position opposite to the main passage hole, and a secondary through hole located at a position opposite to the secondary passage hole and extended to outside of the ball valve, so that when the ball is rotated to a position where the secondary flow hole, the secondary passage hole, and the secondary through hole communicate with each other, a fluid contained in a pipe is introduced to outside of the ball valve, so that the fluid contained the pipe can be sampled without having to dismantle the pipe, thereby facilitating a sampling work in each section of the pipe.

Preferably, the two ball pads mounted at two sides of the ball valve may be simultaneously provided with a main passage hole and a second passage hole located at a position opposite to the main flow hole and the secondary flow hole and having a shape the same as that of the main flow hole and the secondary flow hole.

Further benefits and advantages of the present invention will become apparent after a careful reading of the detailed description with appropriate reference to the accompanying drawings.

DETAILED DESCRIPTION OF THE INVENTION

Figure 1:
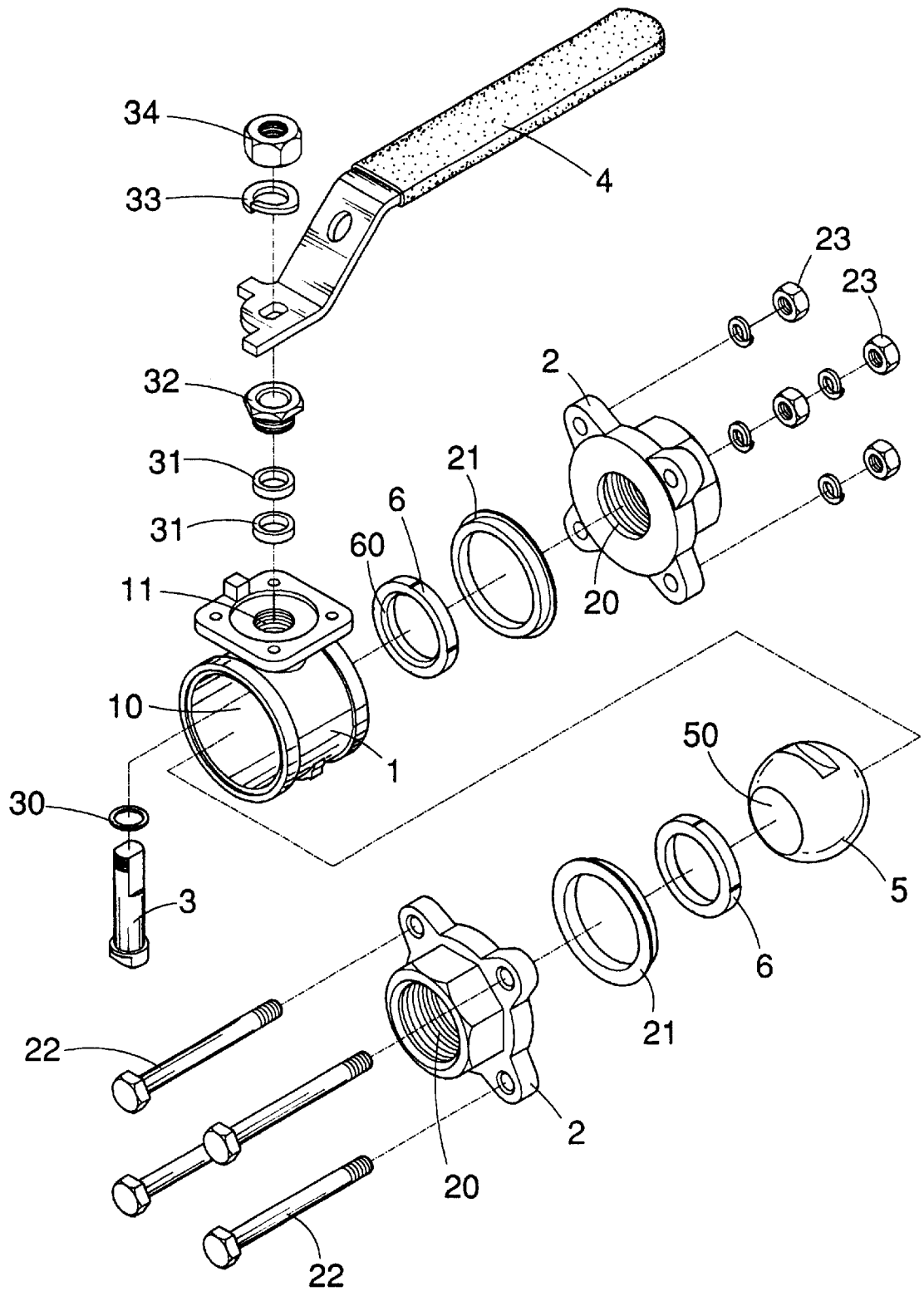
FIG. 1 is an exploded perspective view of a conventional ball valve structure in accordance with the prior art.
Figure 2:
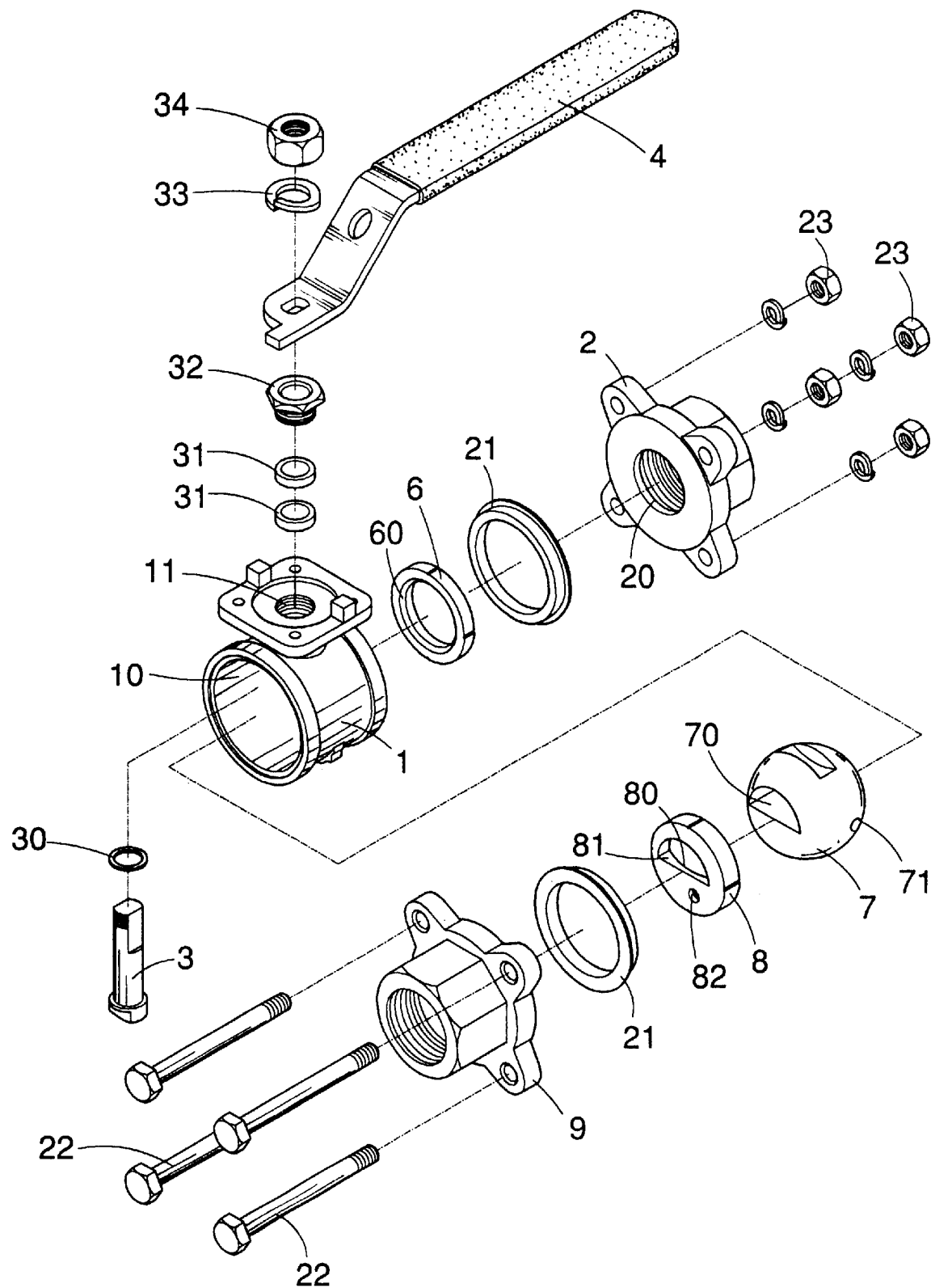
FIG. 2 is an exploded perspective view of a ball valve structure improvement in accordance with the present invention.
Figure 3:
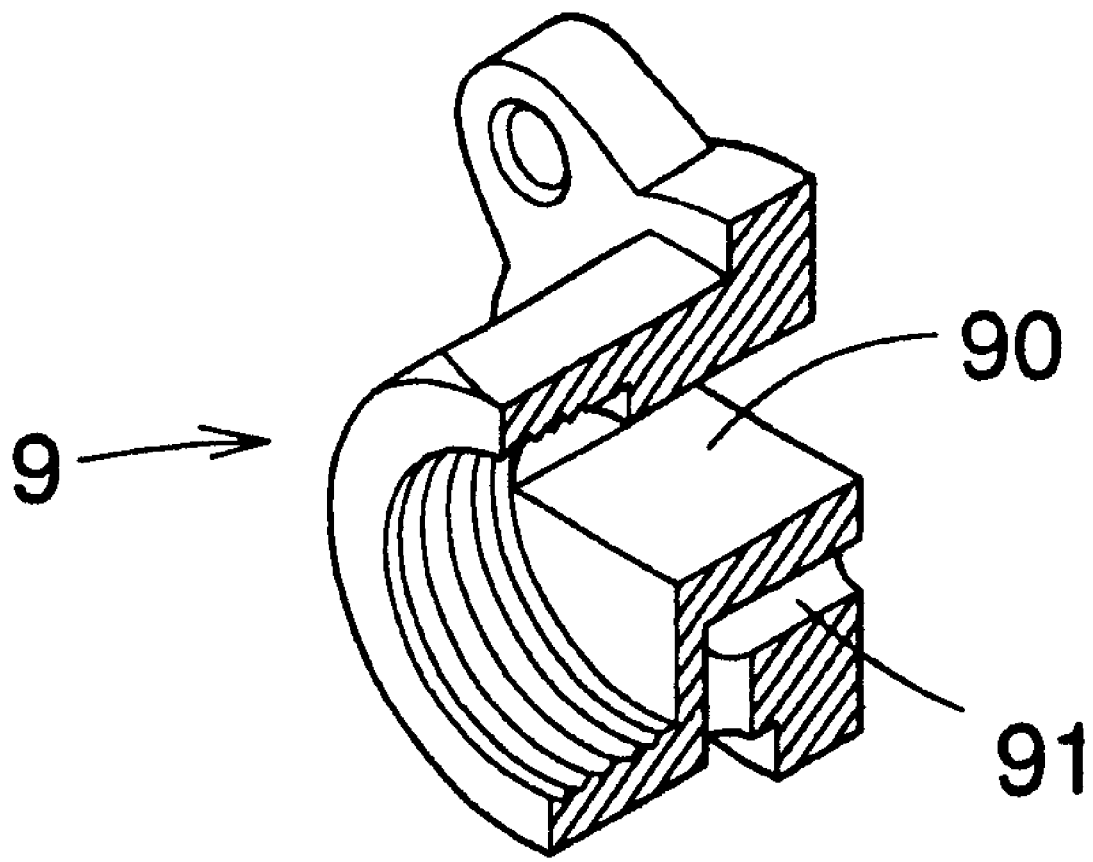
FIG. 3 is a perspective cross-sectional view of a side cover of the ball valve structure improvement in accordance with the present invention.
Figure 4:
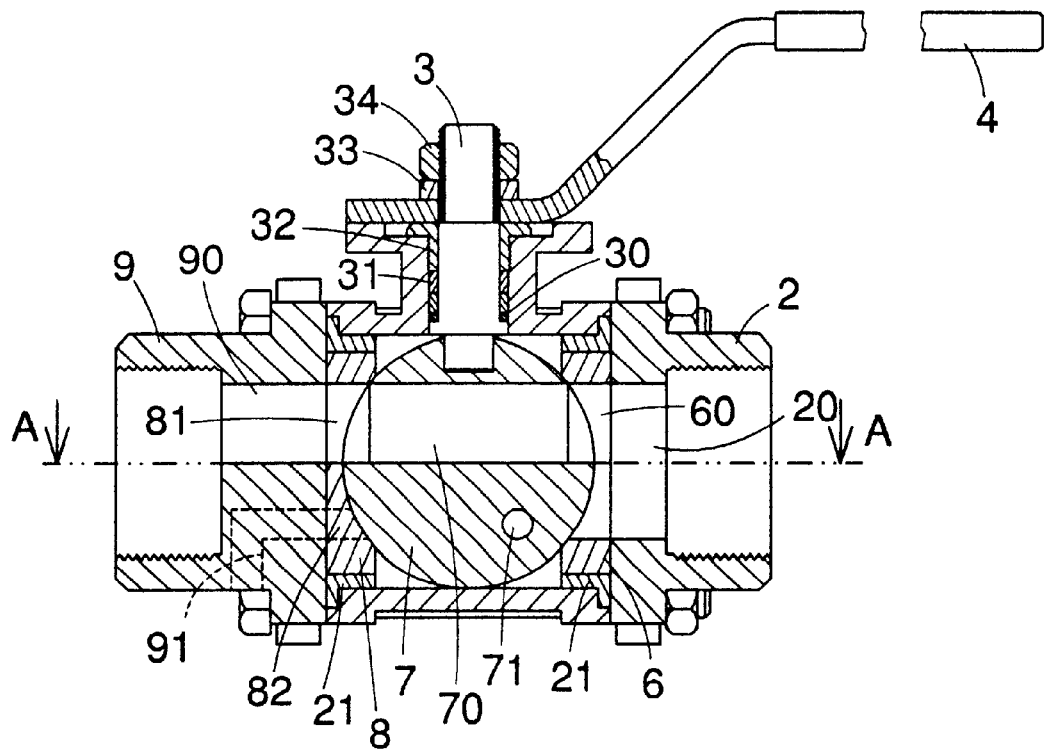
FIG. 4 is a front plan cross-sectional assembly view of the ball valve structure improvement as shown in FIG. 2.

Referring to the drawings and initially to FIGS. 2–4, a ball valve structure improvement in accordance with the present invention comprises a body 1, a first side cover 2, a second side cover 9, a central shaft 3, a handle 4, a ball 7, a first ball pad 6, and a second ball pad 8. The first ball pad 6 and the second ball pad 8 are respectively mounted on two sides of the ball 7. The central shaft 3 has a first end extended into the body 1 and inserted into the ball 7 for rotating the ball 7, and a second end extended outward from the body 1 and secured with the handle 4. The first side cover 2 and the second side cover 9 are respectively mounted on two sides of the body 1 for sealing the ball 7, the first ball pad 6, and the second ball pad 8 in the body 1. The above-mentioned structure is conventional and will not be further described in detail.

The improvement of the present invention is described as follows.

A semi-circular larger main flow hole 70 is defined through the ball 7, and a smaller secondary flow hole 71 is eccentrically defined through the ball 7, wherein the secondary flow hole 71 is perpendicular to and is not communicated with the main flow hole 70. The second ball pad 8 mounted on one side of the ball 7 defines a main passage hole 81 located at a position opposite to the main flow hole 70, and a secondary passage hole 82 located at a position opposite to the secondary flow hole 71. The main passage hole 81 and the secondary passage hole 82 have the same shape as the main flow hole 70 and the secondary flow hole 71 respectively. The second ball pad 8 has one side facing the ball 7 and formed with an arc-shaped face 80 so that the ball 7 can be tightly inserted therein. The second side cover 9 mounted beside the 24 second ball pad 8 defines a main through hole 90 located at a position opposite to the main passage hole 81, and a secondary through hole 91 located at a position opposite to the secondary passage hole 82 and extended to outside of the ball valve.

Figure 5:
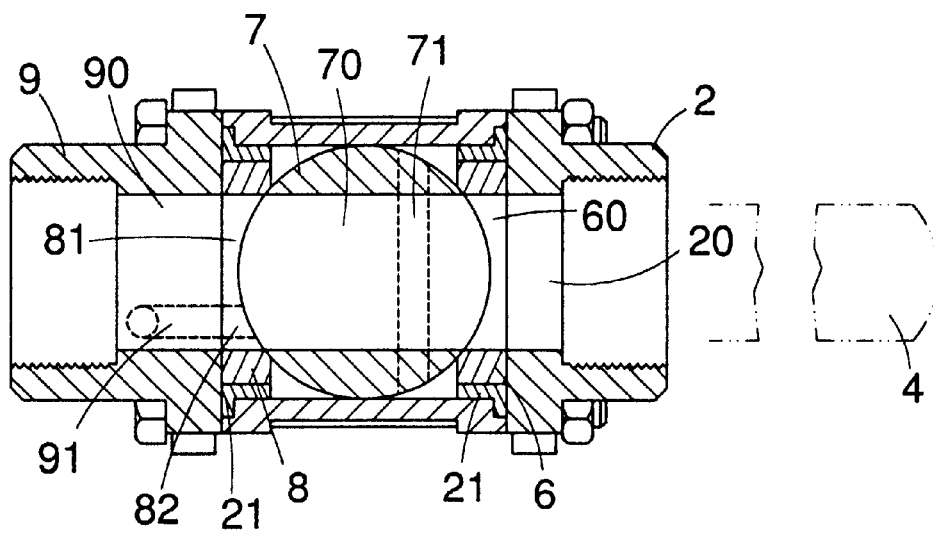
FIG. 5 is a cross-sectional assembly view of the ball valve structure improvement along the line A—A as shown in FIG. 4.

Referring to FIGS. 4 and 5, when the handle 4 is rotated toward the direction of the pipe, the ball 7 is rotated by the central shaft 3 to a position where the main flow hole 70 communicates with the main passage hole 81, so that the pipe is disposed at an open state.

Figure 6:
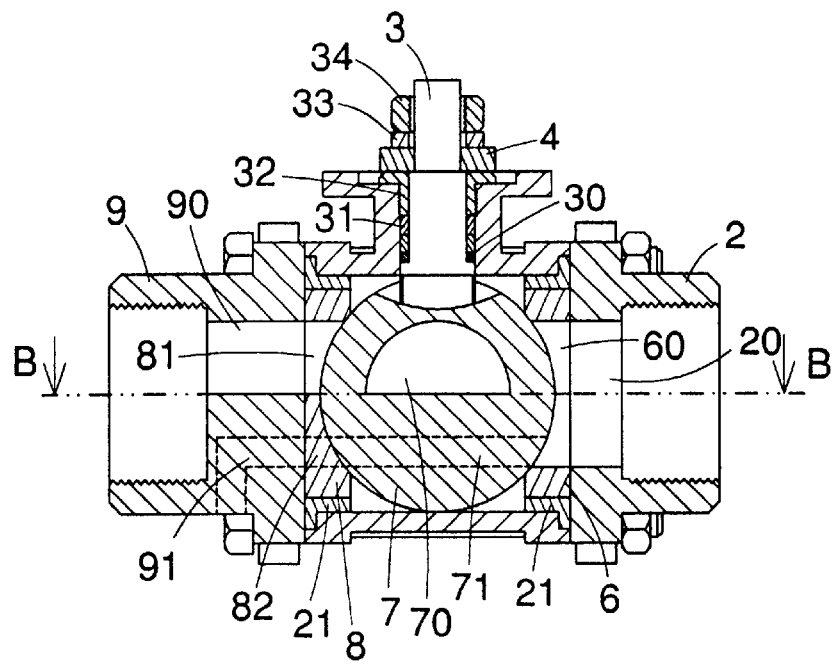
FIG. 6 is a schematic operational view of the ball valve structure improvement as shown in FIG. 4.
Figure 7:
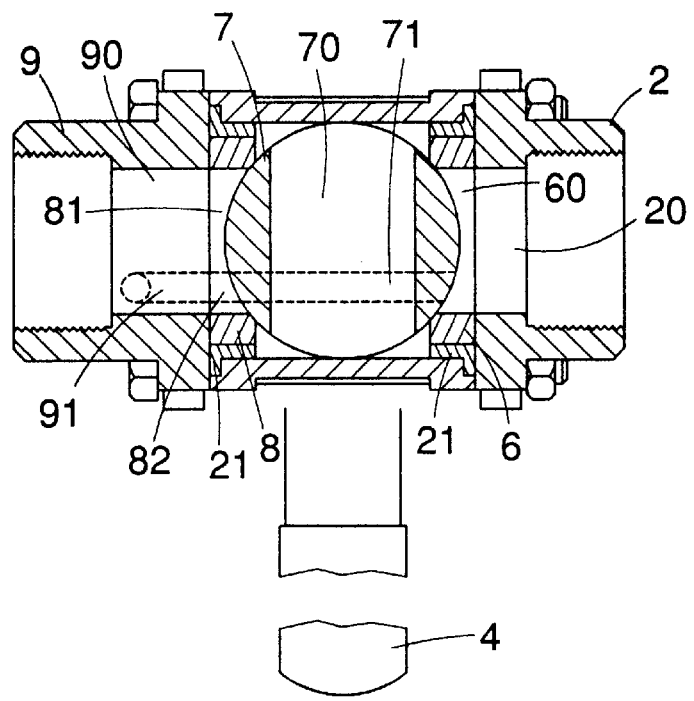
FIG. 7 is a cross-sectional assembly view of the ball valve structure improvement along the line B—B as shown in FIG. 6.

Referring to FIGS. 6 and 7, when the handle 4 is rotated clockwise to the position perpendicular to the pipe, the ball 7 is rotated by the central shaft 3 to a position where the main flow hole 70 is not communicated with the main passage hole 81, so that the pipe is disposed at a closed state. At the same time, the secondary flow hole 71 communicates with the secondary passage hole 82, whereby the sampling fluid conduit is disposed at an open state, so that the fluid contained in the pipe is introduced to outside of the ball valve, so that the fluid contained the pipe can flow outward through the secondary through hole 91 of the second side cover 9 to be used for sampling or to be connected to other inspection pipe, thereby achieving the sampling and inspecting effects.

Figure 8:
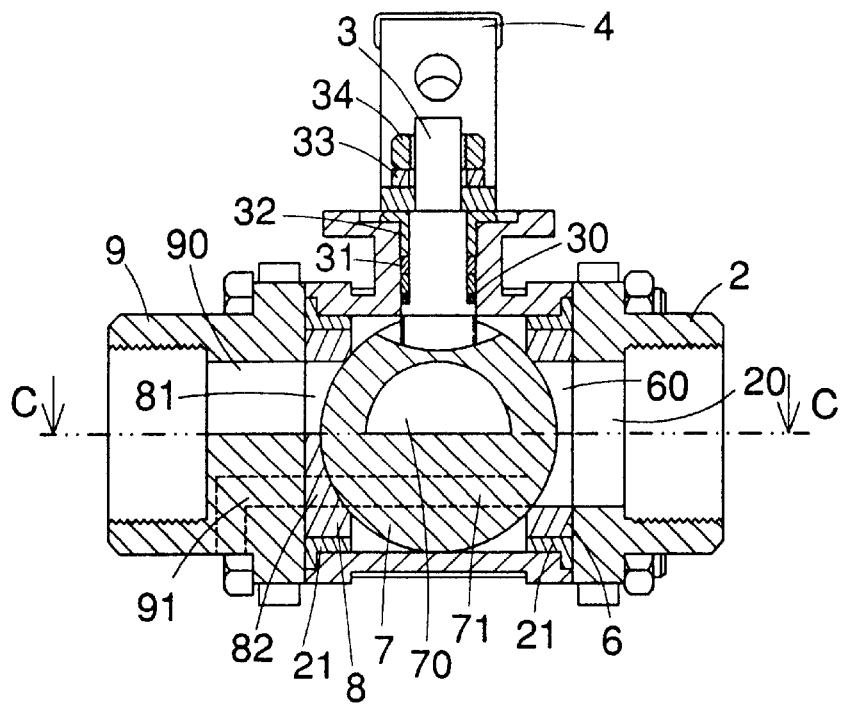
FIG. 8 is a schematic operational view of the ball valve structure improvement as shown in FIG. 4.
Figure 9:
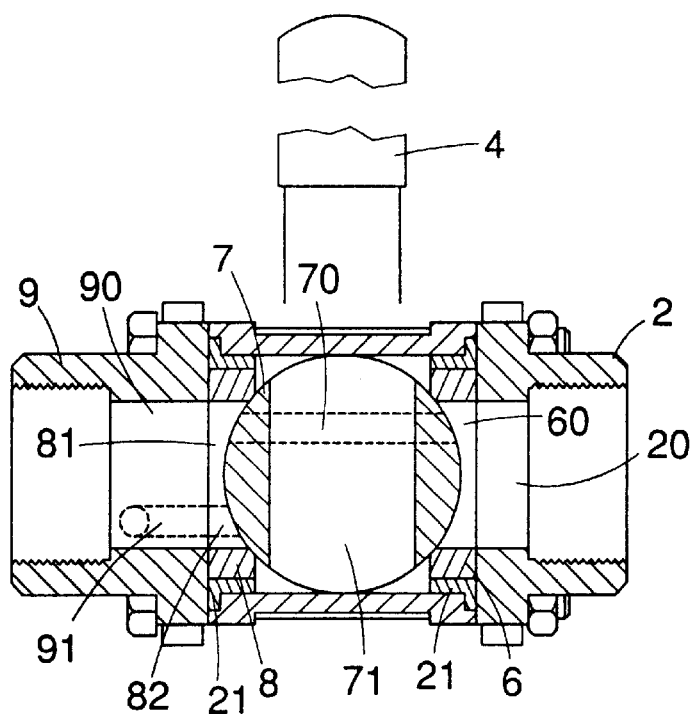
FIG. 9 is a cross-sectional assembly view of the ball valve structure improvement along the line C—C as shown in FIG. 8.

Referring now to FIGS. 8 and 9, when the handle 4 is rotated in the counterclockwise direction to the position perpendicular to the pipe, the ball 7 is rotated by the central shaft 3 to a position where the main flow hole 70 is not communicated with the main passage hole 81, so that the pipe is disposed at a closed state. At the same time, the secondary flow hole 71 is not communicated with the secondary passage hole 82, so that the sampling fluid conduit is also disposed at a closed state.

Accordingly, the ball valve structure improvement of the present invention has the function of a branch flow, so as to control the fluid conduit and the sampling fluid conduit to be disposed at an open state or closed state, so that the fluid contained the pipe can be sampled without having to dismantle the pipe, thereby facilitating the sampling work in each section of the pipe, so that the sampling work in each section of the pipe can be executed simply, quickly and conveniently.

While the preferred embodiment of the present invention has been shown and described, it will be apparent to those skilled in the art that various modifications may be made in the embodiment without departing from the spirit of the present invention. Such modifications are all within the scope of the present invention.

What is claimed is:

1. A ball valve structure improvement, comprising: a body (1), a first side cover (2), a second side cover (9), a central shaft (3), a handle (4), a ball (7), a first ball pad (6), and a second ball pad (8), said first ball pad (6) and said second ball pad (8) respectively mounted on two sides of said ball (7), said central shaft (3) having a first end extended into said body (1) and inserted into said ball (7) for rotating said ball (7), and a second end extended outward from said body (1) and secured with said handle (4), said first side cover (2) and said second side cover (9) respectively mounted on two sides of said body (1), for sealing said ball (7), said first ball pad (6), and said second ball pad (8) in said body (1), wherein, a main flow hole (70) is defined through said ball (7), a secondary flow hole (71) is eccentrically defined through said ball (7), said secondary flow hole (71) is perpendicular to and is not communicated with said main flow hole (70), said second ball pad (8) mounted on one side of said ball (7) defines a main passage hole (81) located at a position opposite to said main flow hole (70), and a secondary passage hole (82) located at a position opposite to said secondary flow hole (71), said second side cover (9) mounted beside said second ball pad (8) defines a main through hole (90) located at a position opposite to said main passage hole (81), and a secondary through hole (91) located at a position opposite to said secondary passage hole (82) and extended to outside of said ball valve, so that when said ball (7) is rotated to a position where said secondary flow hole (71), said secondary passage hole (82), and said secondary through hole (91) communicate with each other, a fluid contained in a pipe is introduced to outside of said ball valve, so that said fluid contained said pipe can be sampled without having to dismantle said pipe, thereby facilitating a sampling work in each section of said pipe.

2. The ball valve structure improvement in accordance with claim 1, wherein said two ball pads mounted at two sides of said ball valve may be simultaneously provided with a main passage hole and a second passage hole located at a position opposite to said main flow hole and said secondary flow hole and having a shape the same as that of said main flow hole and said secondary flow hole.

* * * * *